(12) United States Patent
Bjaerum et al.

(10) Patent No.: US 6,863,655 B2
(45) Date of Patent: Mar. 8, 2005

(54) ULTRASOUND DISPLAY OF TISSUE, TRACKING AND TAGGING

(75) Inventors: Steinar Bjaerum, Horton (NO); Bjorn Olstad, Stathelle (NO); Kjell Kristoffersen, Oslo (NO)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 10/064,085

(22) Filed: Jun. 10, 2002

(65) Prior Publication Data

US 2003/0013964 A1 Jan. 16, 2003

Related U.S. Application Data

(60) Provisional application No. 60/297,572, filed on Jun. 12, 2001.

(51) Int. Cl.[7] .................................................. A61B 8/06
(52) U.S. Cl. ....................................... 600/442; 600/449
(58) Field of Search ................................ 600/441, 437, 600/443, 438, 450, 440, 453, 444, 456, 449; 128/916

(56) References Cited

U.S. PATENT DOCUMENTS

| | | | | |
|---|---|---|---|---|
| 4,382,184 A | * | 5/1983 | Wernikoff .................... | 378/37 |
| 5,224,481 A | * | 7/1993 | Ishihara et al. ............. | 600/443 |
| 5,241,473 A | * | 8/1993 | Ishihara et al. ............. | 600/443 |
| 5,355,887 A | * | 10/1994 | Iizuka et al. ................ | 600/440 |
| 5,415,171 A | * | 5/1995 | Goh et al. ................... | 600/443 |
| 5,462,058 A | * | 10/1995 | Yamada et al. ............. | 600/454 |
| 5,469,850 A | * | 11/1995 | Iizuka et al. ................ | 600/440 |
| 5,533,510 A | * | 7/1996 | Koch et al. .................. | 600/443 |
| 5,544,656 A | * | 8/1996 | Pitsillides et al. .......... | 600/450 |
| 5,622,174 A | * | 4/1997 | Yamazaki .................... | 600/441 |
| 5,628,321 A | | 5/1997 | Scheib et al. | |
| 5,797,843 A | * | 8/1998 | Fitch et al. .................. | 600/437 |
| 5,820,561 A | * | 10/1998 | Olstad et al. ................ | 600/453 |
| 5,839,441 A | * | 11/1998 | Steinberg .................... | 600/450 |
| 5,846,202 A | | 12/1998 | Ramamurthy et al. | |
| 5,860,927 A | * | 1/1999 | Sakaguchi et al. .......... | 600/453 |
| 5,871,019 A | * | 2/1999 | Belohlavek ................. | 600/450 |
| 5,910,119 A | | 6/1999 | Lin | |
| RE37,088 E | * | 3/2001 | Olstad et al. ................ | 600/440 |
| 6,346,124 B1 | * | 2/2002 | Geiser et al. ................ | 600/450 |
| 6,491,636 B2 | * | 12/2002 | Chenal et al. ............... | 600/450 |
| 6,517,485 B2 | * | 2/2003 | Torp et al. ................... | 600/438 |
| 6,527,717 B1 | * | 3/2003 | Jackson et al. ............. | 600/437 |
| 6,579,240 B2 | * | 6/2003 | Bjaerum et al. ............ | 600/447 |
| 6,592,522 B2 | * | 7/2003 | Bjaerum et al. ............ | 600/443 |

* cited by examiner

*Primary Examiner*—Ali Imam
(74) *Attorney, Agent, or Firm*—McAndrews, Held & Malloy, Ltd.; Peter J. Vogel; Michael A. Dellapenna

(57) ABSTRACT

An ultrasound machine that generates a pattern of indicia corresponding to tracked moving structure, such as a cardiac wall tissue that is displayed on a monitor. The pattern of indicia is generated by displaying a set of tagging symbols related to the tracked movement of the structure over a time period by an apparatus comprising a front-end that generates received signals in response to backscattered ultrasound waves. A Doppler processor generates a spatial set of signals values representing movement within the structure. A non-Doppler processor generates a set of parameter signals representing a spatial set of B-mode values within the structure. A host processor embodies a tracking function to generate a set of tracked movement parameter profiles and motion parameter profiles over a time period corresponding to anatomical locations associated with the set of tagging symbols. A display processor overlays the set of tagging symbols onto an image of the moving structure on a monitor, such as B-mode, showing a pattern of indicia that allows visualization of the expansion and contraction of the moving structure in real-time over the time period.

22 Claims, 6 Drawing Sheets

MYOCARDIUM TISSUE
STRUCTURE *105*

APICAL 4-CHAMBER
VIEW OF HEART

ULTRASOUND DISPLAY OF TISSUE, TRACKING AND TAGGING

CROSS REFERENCE TO RELATED APPLICATIONS

The applicants claimed priority based on provisional application No. 60/297,572 filed Jun. 12, 2001 in the names of Bjorn Olstad, Steinar Bjaerum, and Kjell Kristoffersen.

BACKGROUND OF INVENTION

Certain embodiments of the present invention relate to an ultrasound machine for tracking and tagging moving structure. More particularly, certain embodiments relate to the tracking and tagging of moving cardiac tissue for visualization of expansion and contraction processes of the tissue.

Echocardiography is a branch of the ultrasound field that is currently a mixture of subjective image assessment and extraction of key quantitative parameters of cardiac wall function has been hampered by a lack of well-established parameters that may be used to increase the accuracy and objectivity in the assessment of, for example, coronary artery diseases. Stress echo is such an example. It has been shown that the subjective part of wall motion scoring in stress echo is highly dependent on operator training and experience. It has also been shown that inter-observer variability between echo-centers is unacceptably high due to the subjective nature of the wall motion assessment.

Much technical and clinical research has focused on the problem and has aimed at defining and validating quantitative parameters. Encouraging clinical validation studies have been reported, which indicate a set of new potential parameters that may be used to increase objectivity and accuracy in the diagnosis of, for instance, coronary artery diseases. Many of the new parameters have been difficult or impossible to assess directly by visual inspection of the ultrasound images generated in real-time. The quantification has required a post-processing step with tedious, manual analysis to extract the necessary parameters.

Assessment of the expansion and contraction of moving anatomical structure is no exception. Time intensive post-processing techniques or complex, computation intensive real time techniques have been tried in the prior art.

A need exists for a simpler, real-time technique for visualization and assessment of cardiac wall motion by viewing the expansion and contraction of the cardiac tissue.

SUMMARY OF INVENTION

An embodiment of the present invention provides an ultrasound system for generating an image responsive to moving cardiac structure by tracking and tagging the structure in order to directly visualize the expansion and contraction processes of the structure within the image on a display in real time.

An apparatus is provided in an ultrasound machine for generating an image responsive to moving structure of a subject and for generating a representation of displacement of the moving structure. In such an environment, a front-end is arranged to transmit ultrasound energy into the structure and then to generate received signals in response to ultrasound waves backscattered from the structure over a period of time. A display is arranged to display the image of the moving structure in response to the received signals. A user interface is arranged to enable a user of the machine to overlay the image on the display with a first pattern of indicia corresponding to sampled anatomical locations within the moving structure. A processor is responsive to the received signals to generate parameter signals representing displacement of the anatomical locations corresponding to the pattern of indicia during at least a portion of the time period and is responsive to the parameter signals to generate a second pattern of indicia corresponding to the displacement of the anatomical locations and to overlay the second pattern of indicia on the image on the display to provide real-time visualization of the displacement.

A method is also provided in an ultrasound machine for generating an image responsive to moving structure of a subject and for generating a representation of displacement of the moving structure. In such an environment, the method comprises transmitting ultrasound waves into the structure and generating received signals in response to ultrasound waves backscattered from the structure over a period of time. The image of the moving structure is displayed in response to the received signals. A user of the machine is able to overlay the image with a first pattern of indicia corresponding to sampled anatomical locations within the moving structure. Parameter signals are generated representing displacement of the anatomical locations corresponding to the pattern of indicia during at least a portion of the time period in response to the received signals. A second pattern of indicia is generated corresponding to the displacement of the anatomical locations in response to the parameter signals and is overlaid on the image to provide real-time visualization of the displacement.

Certain embodiments of the present invention afford an approach to visualize, by using the foregoing techniques, the contraction and expansion of moving anatomical structure in real-time with a degree of convenience and accuracy previously unattainable in the prior art.

The foregoing summary, as well as the following detailed description of certain embodiments of the present invention, will be better understood when read in conjunction with the appended drawings. It should be understood, however, that the present invention is not limited to the arrangements and instrumentality shown in the attached drawings.

DETAILED DESCRIPTION

An embodiment of the present invention enables tracking of moving structure and real-time visualization of contraction and expansion of the moving structure. As used herein, structure means non-liquid and non-gas matter, such as cardiac wall tissue.

An embodiment of the present invention offers improved, real-time visualization and assessment of the displacement of wall tissue. Displacement may be, for example, distance moved by the structure or deformation of the moving structure. The moving structure is characterized by a pattern of indicia (set of tagging symbols) overlaid onto an image of the moving structure. The characterization of the moving tissue is accomplished, in part, by generating a set of signal values derived from movement of the structure, such as mean longitudinal velocity.

Figure 1:
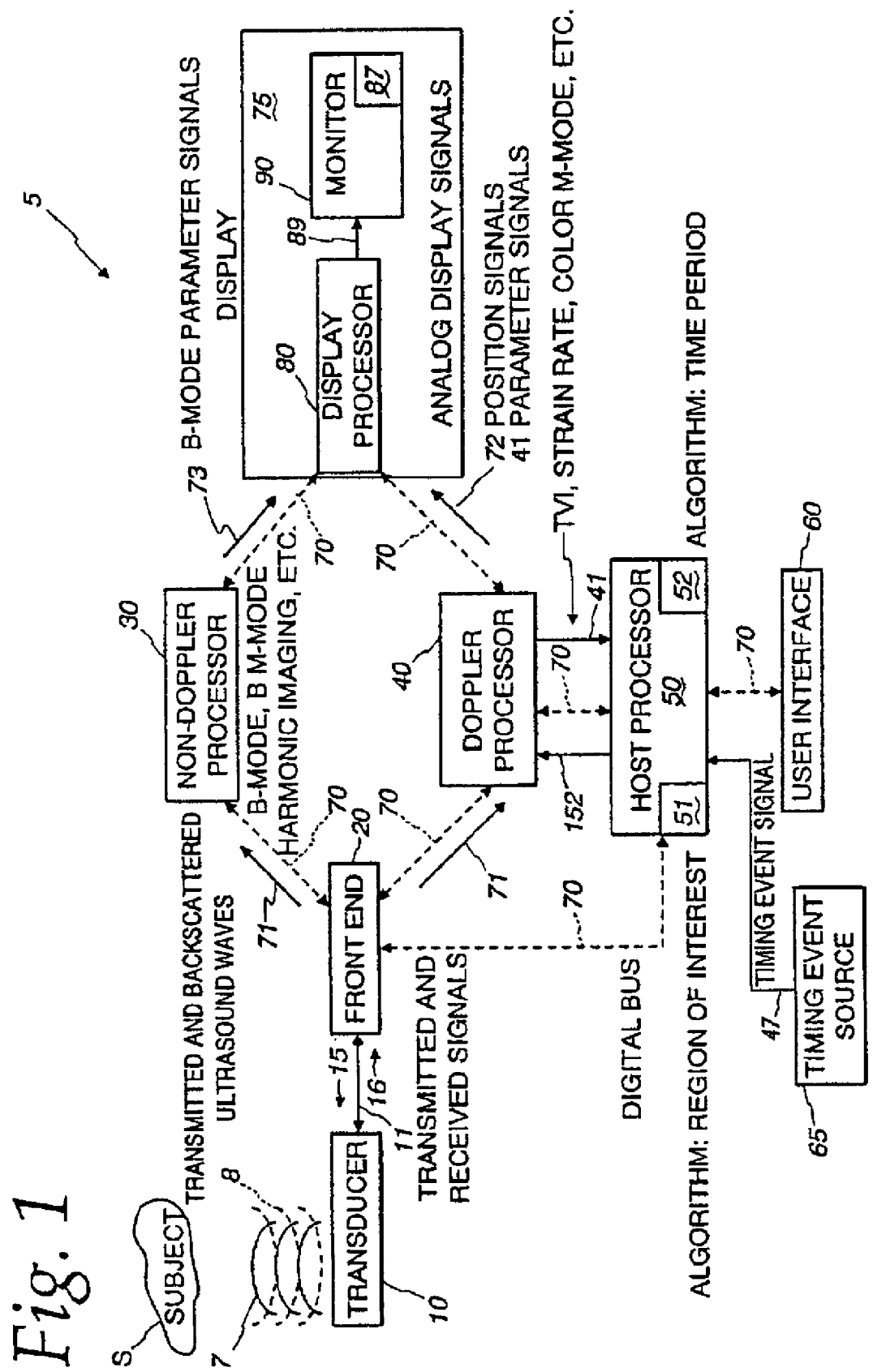
FIG. 1 is a schematic block diagram of an ultrasound machine made in accordance with an embodiment of the present invention.

FIG. 1 is a schematic block diagram of an embodiment of the present invention comprising an ultrasound machine 5. A transducer 10 is used to transmit ultrasound waves 7 (solid curves in FIG. 1) into a subject S by converting electrical analog signals 15 to ultrasonic energy, and to receive ultrasound waves 8 (dashed curves in FIG. 1) backscattered from the subject S by converting ultrasonic energy to analog electrical signals 16.

A front-end 20 comprising a receiver, transmitter, and beamformer, is used to create the transmitted waveforms, beam patterns and receiver filtering techniques used for the various imaging modes. Front-end 20 performs the functions by converting digital data to analog data and vice versa. Front-end 20 interfaces at an analog interface to transducer 10 and interfaces at a digital interface over a digital bus 70 to a non-Doppler processor 30 and a Doppler processor 40 and a host processor 50. Digital bus 70 may comprise several digital sub-buses, each sub-bus having its own unique configuration and providing digital data interfaces to various parts of the ultrasound machine 5.

Non-Doppler processor 30 comprises amplitude detection functions and data compression functions used for imaging modes such as B-mode, B M-mode, and harmonic imaging. Doppler processor 40 comprises clutter filtering functions and movement parameter estimation functions used for imaging modes such as tissue velocity imaging (TVI), strain rate imaging (SRI), and color M-mode. The two processors, 30 and 40, accept received signal digital data 71 from the front-end 20, process the data into sets of signal values 41 (FIG. 3), and pass the values to processor 50 and/or a display 75 over digital bus 70. The estimated signal values may be created using the received signals 71 in frequency bands centered at the fundamental, harmonics, or sub-harmonics of the transmitted signals in a manner known to those skilled in the art.

Display 75 comprises scan-conversion functions, color mapping functions, and tissue/flow arbitration functions, performed by a display processor 80 which accepts digital signals 41 (FIG. 3) and 73 from processors 30 and 40. Digital data 72, representing a location of a pattern of indicia 155, is accepted from host processor 50. Display processor 80 processes, maps, and formats the digital data for display, converts the digital display data to analog display signals 89, and passes the analog display signals 89 to a monitor 90.

Monitor 90 accepts the analog display signals 89 from display processor 80 and displays the resultant image 87 to the operator on monitor 90.

A user interface 60 allows user commands to be input by the operator to the ultrasound machine 5. User interface 60 comprises a keyboard, mouse, switches, knobs, buttons, track ball, and on screen menus (not shown).

Host processor 50 is the main, central processor of the ultrasound machine 5 and interfaces to various other parts of the ultrasound machine 5 through digital bus 70. Host processor 50 executes the various data algorithms and functions for the various imaging modes. Digital data and commands may be transmitted and received between the host processor 50 and other various parts of the ultrasound machine 5. The functions performed by processor 50 may be performed by multiple processors or may be integrated into processors 30, 40, or 80, or any combination thereof.

Figure 2:
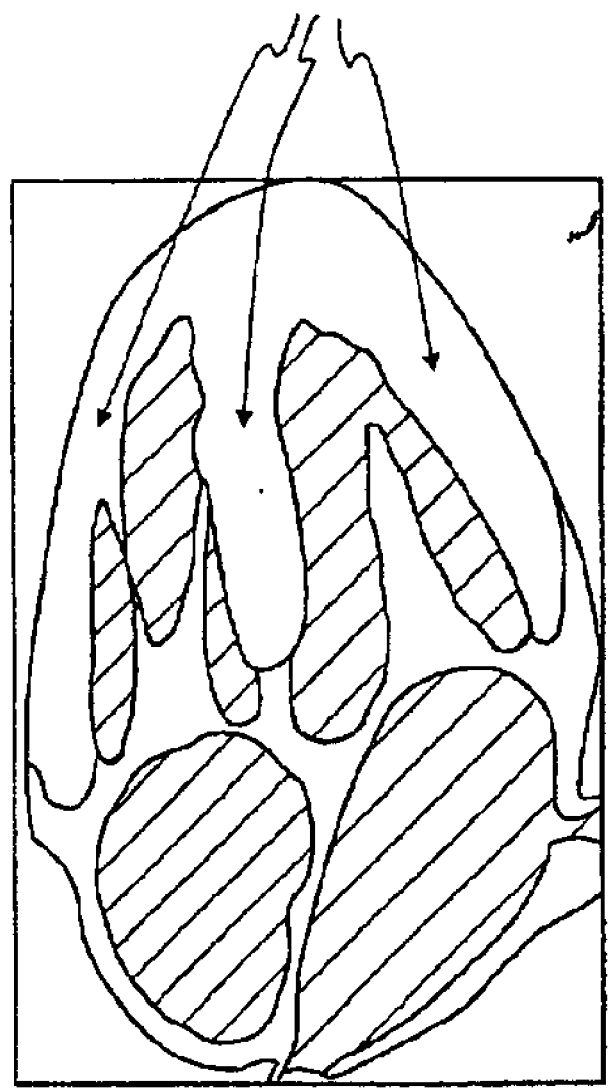
FIG. 2 is a schematic cross-sectional view of the human heart including myocardium tissue.
Figure 3:
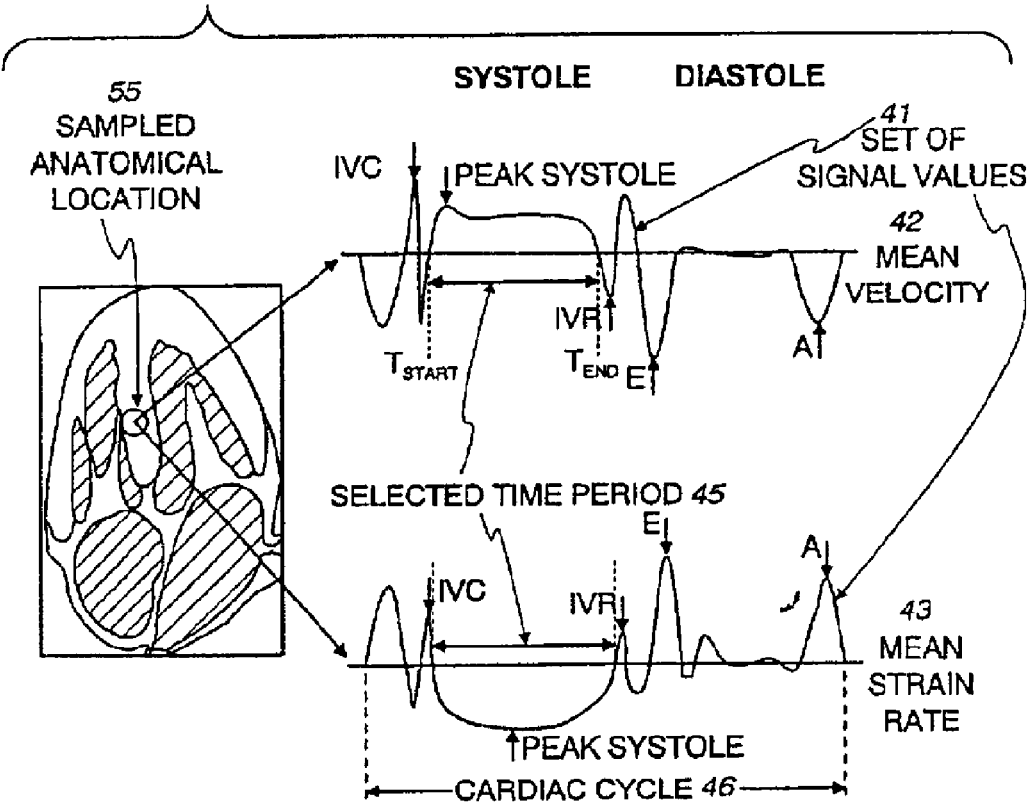
FIG. 3 is a schematic cross-sectional view of the heart shown in FIG. 2 also graphically representing mean velocity and mean strain rate profiles as a function of time, measured longitudinally in an apical view for a sampled anatomical location in accordance with an embodiment of the present invention.

In an embodiment of the present invention, an operator uses transducer 10 to transmit ultrasound energy into the appropriate anatomical structure, such as cardiac tissue 105 (see FIG. 2), of the subject in an imaging mode (such as TVI mode interleaved with B-mode) that yields a desired set of signal values 41 (see FIG. 3) of the anatomical structure 105. As shown in FIG. 3, the set of signal values 41 typically comprises longitudinal estimates of mean tissue velocity 42 and mean tissue strain rate 43.

Ultrasound energy is received into transducer 10 and signals are received into front-end 20 in response to ultrasound waves 8 backscattered from the structure 105. The received signals 71 are sent from front-end 20 to Doppler processor 40 and Non-Doppler processor 30 over digital bus 70. Many sets of signal values 41 (such as mean velocity 42) and B-mode signals 73 (such as amplitude) are generated from the received signals 71 over a segmented time period 45 (FIG. 3) by Doppler processor 40 and Non-Doppler processor 30.

The operator selects, through the user interface 60, a desired time interval 45 to process, such as systole, which is a sub-interval of the cardiac cycle 46 (see FIG. 3).

The time interval is designated by $T_{start}$ and $T_{end}$. The time interval is determined from a timing signal 47 generated from a timing event source 65 (FIG. 1) and/or from characteristic signatures of the set of signal values 41. An example of such a timing signal is an electrocardiogram (ECG) signal (see FIG. 4). Those skilled in ultrasound also know how to derive timing events from signals of other sources such as a phonocardiogram signal, a pressure wave signal, a pulse wave signal, or a respiratory signal. Ultrasound modalities such as spectrum Doppler or M-modes may also be used to obtain timing information.

$T_{start}$ is typically selected by the operator as an offset from the R-event in the ECG signal. $T_{end}$ is set such that the time interval covers a selected portion of the cardiac cycle such as systole. It is also possible to select a time period 45 corresponding to the complete cardiac cycle 46. Another possibility is to limit the time period 45 to the systolic time period in order to display a pattern of indicia (tagging symbols) optimized for visualization of systolic motion. Other sub-intervals of the cardiac cycle 46 may also be applied.

FIG. 3 graphically illustrates typical sets of signal values 41 for velocity 42 and strain rate 43 which may be segmented into desired time periods based on signature characteristics. For reference, the profiles in FIG. 3 are annotated with the times corresponding to: IVC=isovolumetric contraction, IVR=isovolumetric relaxation, E=early diastolic velocity, and A=late diastolic velocity. Caution should be taken in the selection of the time interval such that, for example, motion in the IVC or IVR period may be excluded from the analysis, if desired. An automatic function may be implemented to recognize and exclude the unwanted events from the time interval.

Figure 4:
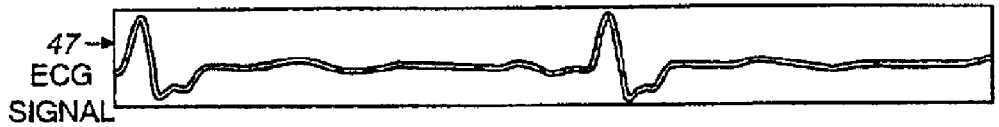
FIG. 4 illustrates an exemplary ECG signal that may be generated by a timing event source and used by the machine in FIG. 1 to identify a time interval in accordance with an embodiment of the present invention.

In other possible embodiments, the time interval may be selected automatically or as a combination of manual and automatic methods. For example, the time period 45 may be determined automatically with an algorithm 52 (see FIG. 1) embedded in host processor 50. The algorithm 52 may use well-known techniques of analyzing the sets of signal values 41, as shown in FIG. 3, looking for key signal signature characteristics and defining a time period 45 based on the characteristics, or similarly, analyzing the ECG signal 47 (FIG. 4).

Figure 5:
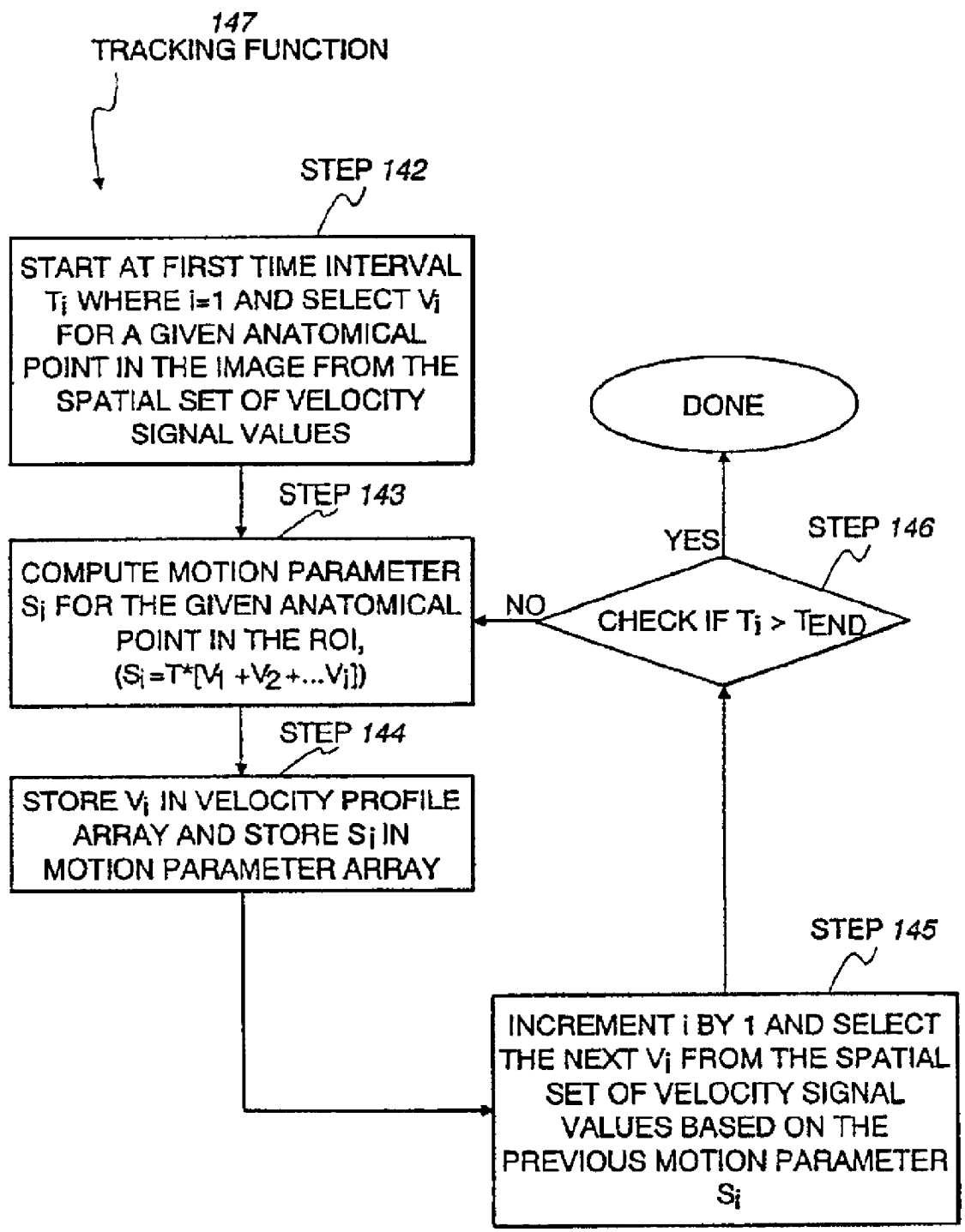
FIG. 5 is a flowchart of the longitudinal tracking function executed by the machine shown in FIG. 1 that generates the graphs shown in FIG. 7 in accordance with an embodiment of the present invention.

The spatial set of signal values 41 representing the movement of the structure 105 is sent from Doppler processor 40 to host processor 50, where a tracking function 147 is applied to the set of signal values 41. FIG. 5 is a flow chart of the tracking function 147.

Figure 6:
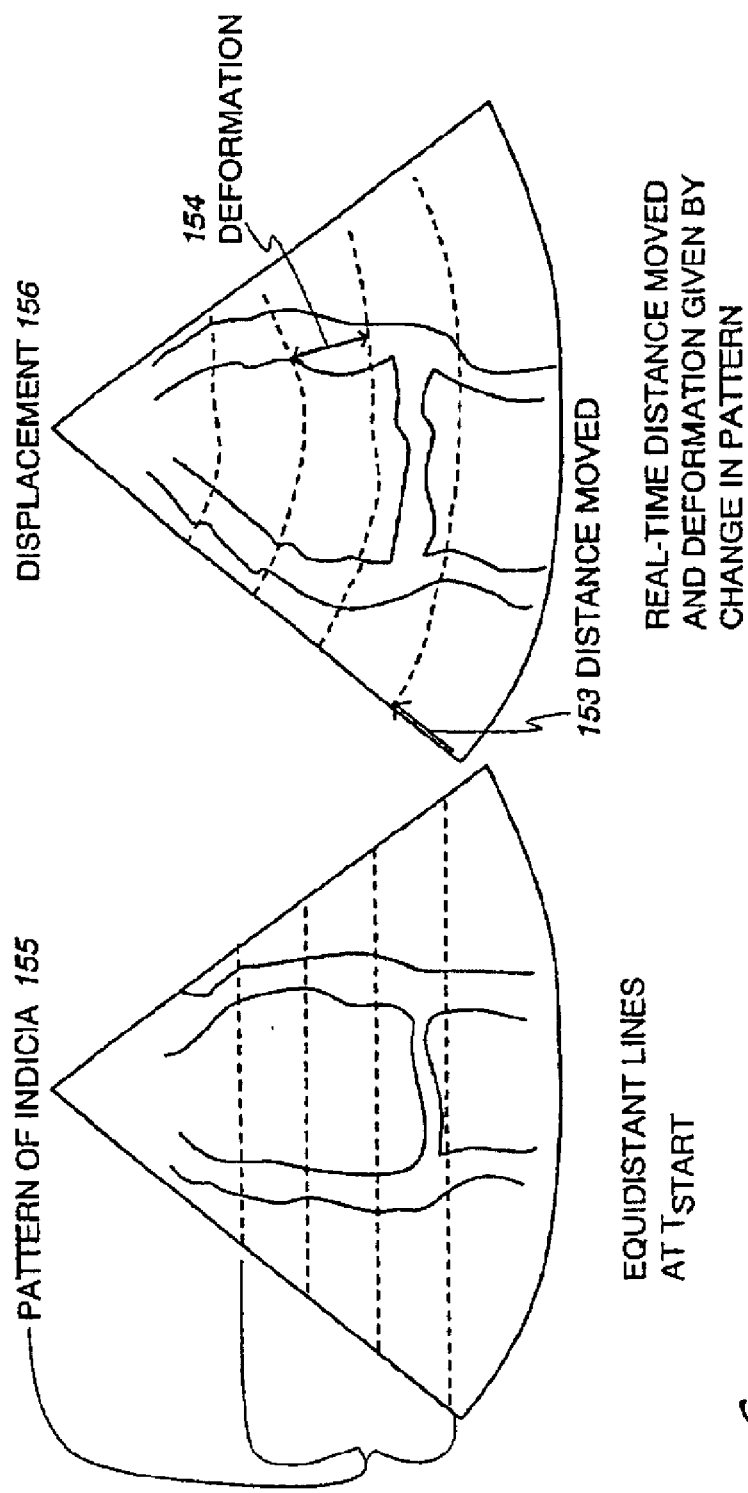
FIG. 6 illustrates displays generated at two different points in time showing tissue displacement with patterns of indicia generated by the machine in FIG. 1 using the function flowcharted in FIG. 5 in accordance with an embodiment of the present invention.

The operator brings up onto the display and positions, through user interface 60, a pattern of indicia 155 (a set of tagging symbols), typically configured in the form of parallel lines or a grid (see FIG. 6). The operator then initiates, through user interface 60, real-time tracking of every sampled anatomical location associated with an element of the pattern of indicia over the selected time period 45 of the cardiac cycle 46. The association is established by host processor 50 where each element of the pattern of indicia 155 is correlated to the anatomical locations beneath the pattern of indicia 155 at time $T_{start}$.

Figure 7:
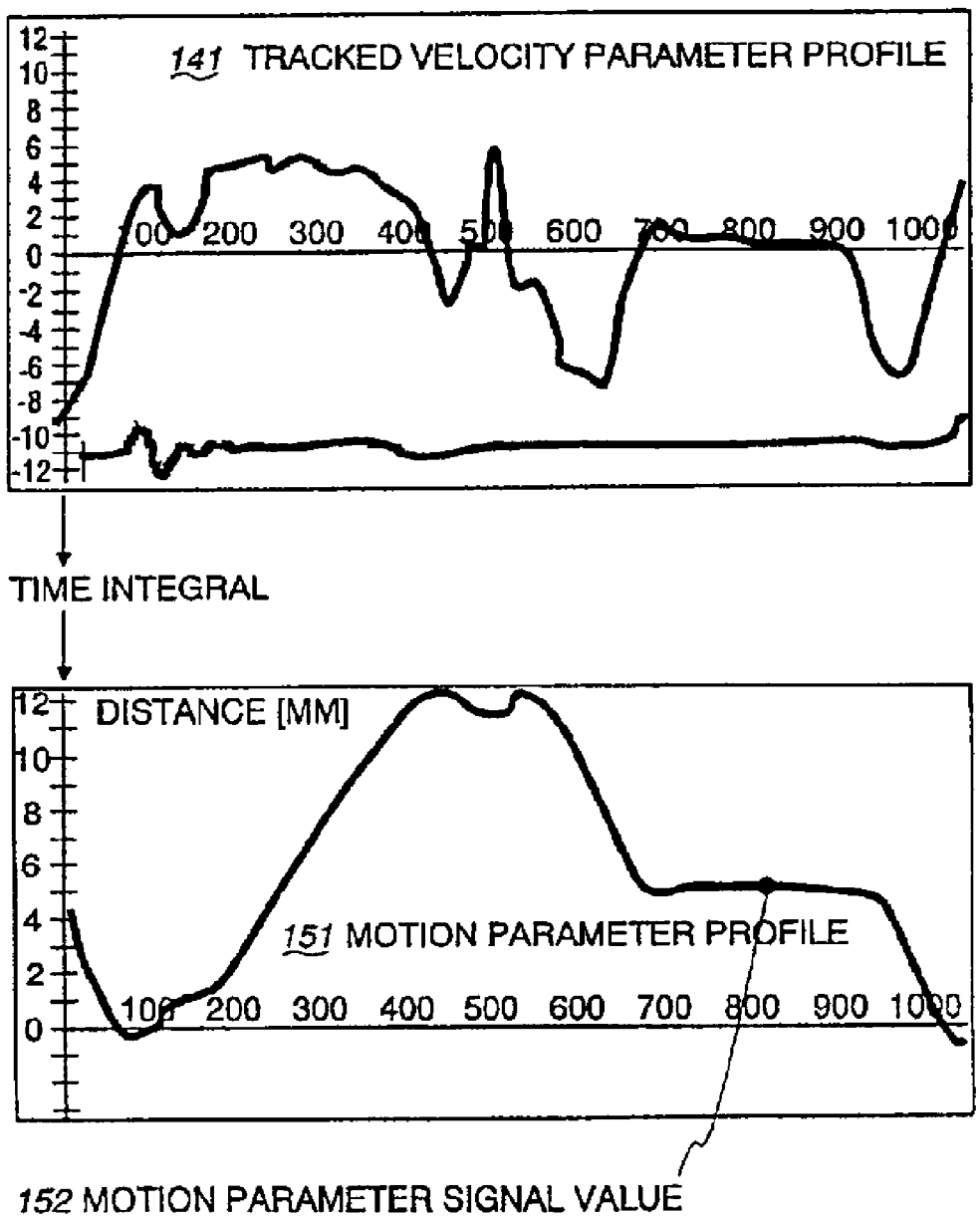
FIG. 7 shows graphs of a tracked velocity parameter profile and a motion parameter profile generated by the tracking function flowcharted in FIG. 5 in accordance with an embodiment of the present invention.

As an introduction to the tracking function 147, a tracked velocity parameter profile 141 ($V_1, V_2, \ldots, V_n$) (FIG. 7) for a given sampled anatomical location 55 in the myocardium 105, is created over the time period $T_{start}$ to $T_{end}$ by converting the spatial set of velocity values 42 into a motion parameter profile 151 in time using host processor 50 by computing the series of time integrals ($S_1, S_2, \ldots, S_n$) where:

$$S_{i=T}*(V_1+V_2+ \ldots +V_i) \qquad \text{[Equation 1]}$$

and where T is the time delay between two consecutive velocity measurements (T is typically based on the frame rate of the imaging mode). $S_i$ (motion parameter signal value) 152 (FIG. 7) is then the longitudinal distance in mm (from reference time $T_{start}$ location) that a sample of tissue in the myocardium has moved at time segment $T_i$, thus allowing the isolated tissue sample to be tracked longitudinally (along the ultrasound beam) over the time interval $T_{start}$ to $T_{end}$ by host processor 50. The start end tracking function 147 estimates the new anatomical location of the tracked sample of tissue after every time segment $T_i$. The element of the pattern of indicia 155 is displayed at that spatial location where the tracking function has determined the corresponding anatomical location has moved to for the next time interval $T_i$. This is done for each tracked location and correlated element of the pattern of indicia in the image. The upper part of FIG. 7 shows a resultant tracked velocity parameter profile 141 of an anatomical location in the image as a function of time for a complete cardiac cycle 46. The lower part of FIG. 7 shows the corresponding resultant longitudinal motion parameter profile 151 (integrated velocity profile, $S_1, S_2, \ldots S_n$) of the same anatomical location in the image. Motion along the ultrasound beam n may be accurately tracked with the technique by generating the appropriate velocity parameter profiles for the corresponding anatomical locations. The tracked velocity parameter profile 141 and motion parameter profile 151 for each anatomical location are stored in the memory of host processor 50 as arrays of values.

Two-dimensional velocity estimation may be used for accurate tracking when a substantial part of the motion of the structure is orthogonal to the beam. Other tracking techniques may be employed as well.

The specific steps of one tracking function 147 are now described for a given anatomical location within the image. A spatial set of mean velocity signal values 42 is estimated so that the motion parameter signal values $S_i$ 152 may be calculated for tracking. The mean velocity values are generated by Doppler processor 40 in a well-known manner.

Referring to FIG. 5, in step 142 of tracking function 147, processor 50 selects $V_i$ for a given anatomical location at a given spatial position in the image from a spatial set of velocity signal values correlated to the location of an element of the pattern of indicia and corresponding to time interval $T_i$ where i=1 ($T_1$ is $T_{start}$).

In step 143 of tracking function 147, processor 50 computes the motion parameter signal value $S_i$ 152 for the given anatomical location by summing mean velocity values as follows:

$$S_i T*(V_1+V_2+ \ldots +V_i) \qquad \text{[Equation 1]}$$

(Note that for i=1, $S_1$=T*$V_1$)

In step 144 of tracking function 147, processor 50 stores $V_i$ in tracked velocity parameter profile array 141 and $S_i$ is stored in motion parameter profile array 151 along with the current spatial position of the anatomical location. Other estimated parameters, such as strain rate 43, corresponding to the tracked anatomical location may be computed and stored in respective tracked profile arrays as well if desired allowing for display of the pattern of indicia 155, for example, overlaid onto a strain rate image. Strain rate is simply computed for each spatial location as it normally is in the SRI mode and the results of the tracking function are used to select the spatial strain rate values that correspond to a tracked anatomical location.

In step 145 of tracking function 147, i is incremented by one (corresponding to the next sample time, T seconds later) and the next $V_i$ is selected from the spatial set of velocity signal values 42 based on the motion parameter signal value $S_i$ 152 previously computed and the previous spatial position of the anatomical location ($S_i$ represents the longitudinal spatial movement in millimeters of the anatomical location over time interval $T_i$=i*T).

Host processor 50 sends the new position information 72 of the pattern of indicia 157 to display processor 80. Display processor 80 re-configures the pattern for display at the new positions. The new position of the pattern is updated and displayed after each new tracked element in the motion parameter profile array is added allowing a constant update of the displayed pattern within the time interval $T_{start}$ to $T_{end}$. The underlying image (e.g. B-mode image) is displayed with the updated pattern of indicia 157 overlaid such that there is spatial alignment between the anatomical locations in the underlying image and the updated pattern of indicia.

In step 146 of tracking function 147, the function checks to see if $T_{end}$ has been end exceeded. If $T_{end}$ has not been exceeded, the function proceeds back to step 143 end and computes the next motion parameter signal value $S_i$ in the series using Equation 1. The iterative process is followed until the full arrays of the tracked velocity parameter profile 141, the motion parameter profile 151, and any other desired parameter profile have been created and stored over the complete time interval $T_{start}$ to $T_{end}$.

The tracking function 147 is performed simultaneously for each anatomical location in the image that corresponds to an element in the pattern of indicia 155 (set of tagging symbols).

FIG. 6 illustrates the function of generating a display of a pattern of indicia 155 (tagging symbols), in rectangular coordinate geometry, overlaid onto a B-mode image of cardiac tissue. The left side of FIG. 6 illustrates a 1-dimensional pattern where equidistant dashed horizontal lines are used to form the pattern corresponding to time $T_{start}$ and is the zero displacement position of the pattern which is positioned by the operator. Another good candidate for the pattern would be to use an equidistant set of lines with constant depth in the polar geometry representation of the ultrasound image. Also, a 2-dimensional grid may be used, which might consist of both horizontal and vertical lines. The right side of FIG. 6 illustrates the display of a frame within the selected time interval $T_{start}$ to $T_{end}$ of the cardiac cycle where the start end positions of the elements of the pattern have been updated to visualize the displacement 156 (distance moved 153 and deformation 154) of the tracked anatomical locations within the cardiac structure 105. The pattern has been changed to correspond to the displacement of the heart tissue. Those skilled in the art will know how to program processor 50 using tracking function 147 (FIG. 5) to achieve the display shown in FIG. 6.

Care should be taken by the operator to adjust the Nyquist frequency of the imaging mode such that aliasing does not occur. With aliasing present in the velocity data, erroneous tracking results occur. Alternatively, well known automatic aliasing correction techniques may be employed. An embodiment of the method may be applied to any imaging mode of the ultrasound machine 5 for moving structure (e.g. B-mode, TVI, SRI, etc).

In summary, certain embodiments of the present invention afford an approach to more easily visualize the displacement of tissue, including expansion and contraction, in a two-dimensional pattern overlaid onto an image of cardiac structure. While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. In an ultrasound machine for generating an image responsive to moving structure of a subject, apparatus representing displacement of the moving structure comprising:
   a front-end arranged to transmit ultrasound waves into the structure and to generate received signals in response to ultrasound waves backscattered from the structure over a selected time period;
   a display arranged to display the image of the moving structure, wherein said display displays at least one pattern of indicia corresponding to sampled anatomical locations within the moving structure, wherein said at least one pattern of indicia comprises at least one set of tagging symbols;
   a user interface enabling a user of the machine to overlay the image on the display with a first pattern of indicia corresponding to sampled anatomical locations within the moving structure; and
   a processor responsive to the received signals to generate parameter signals representing displacement of the anatomical locations corresponding to the pattern of indicia during at least a portion of the selected time period and responsive to the parameter signals to generate a second pattern of indicia corresponding to the displacement of the anatomical locations and to overlay the second pattern of indicia on the image on the display.

2. The apparatus of claim 1 wherein the moving structure comprises cardiac tissue.

3. The apparatus of claim 1 wherein the displacement represents one of distance moved by the moving structure and deformation of the moving structure.

4. The apparatus of claim 1 wherein the image is displayed with a predetermined geometry and the first pattern of indicia comprises a set of lines in the predetermined geometry.

5. The apparatus of claim 4 wherein the set of lines comprises dashed lines.

6. The apparatus of claim 4 wherein the lines are equidistant apart.

7. The apparatus of claim 1 wherein the processor generates the parameter signals by summing a set of signal values representing mean velocities of the moving structure over at least of portion of the time period.

8. The apparatus of claim 1 wherein the time period comprises at least a portion of a cardiac cycle selectable by a user of the machine including at least one of systole, diastole, JYC, LVR, E-wave, and A-wave.

9. The apparatus of claim 8 wherein the portion of the cardiac cycle is selectable from at least one of a set of signal values and a timing event signal comprising at least one of an EGG signal, a phonocardiogram signal, a pressure wave signal, a pulse wave signal, and a respiratory signal.

10. The apparatus of claim 1 wherein the image is one of a B-mode image, a combined B-mode/TVI image, a combined B-mode/SRI image, a TVI image, and an SRI image.

11. In an ultrasound machine for generating an image responsive to moving structure of a subject, a method of representing displacement of the moving structure comprising:
   transmitting ultrasound waves into the structure; generating received signals in response to ultrasound waves backscattered from the structure over a selected time period;
   displaying the image of the moving structure in response to the received signals;
   enabling a user of the machine to overlay the image on the display with a first pattern of indicia corresponding to sampled anatomical locations within the moving structure;
   overlaying said image with at least one pattern of indicia corresponding to sampled anatomical locations within the moving structure;
   generating parameter signals representing displacement of the anatomical locations corresponding to the pattern of indicia during at least a portion of the selected time period in response to the received signals; and
   generating a second pattern of indicia corresponding to the displacement of the anatomical locations in response to the parameter signals and displaying the second pattern of indicia overlaid on the image, wherein said first and second patterns of indicia comprise first and second sets of tagging symbols.

12. The method of claim 11 wherein the moving structure comprises cardiac tissue.

13. The method of claim 11 wherein the displacement represents the distance moved by the moving structure and deformation of the moving structure.

14. The method of claim 11 wherein the image is displayed with a predetermined geometry and the first pattern of indicia comprises a set of lines in the predetermined geometry.

15. The method of claim 14 wherein the set of lines comprises dashed lines.

16. The method of claim 14 wherein the lines are equidistant apart.

17. The method of claim 11 wherein said generating the parameter signals comprises summing a set of signal values representing mean velocities of the moving structure over at least a portion of the time period.

18. The method of claim 11 wherein the time period comprises at least a portion of a cardiac cycle selectable by a user of the machine.

19. The method of claim 18 wherein the portion of the cardiac cycle is selectable from at least one of a set of signal values and a timing event signal comprising at least one of an ECG signal, a phonocardiogram signal, a pressure wave signal, a pulse wave signal, and a respiratory signal.

20. The method of claim 11 wherein the image is one of a B-mode image, a combined B-mode/TVI image, a combined B-mode/SRI image, a TVI image, and an SRI image.

21. A method for visualizing a displacement of tissue, said method comprising:

overlaying, based on user input, a displayed image of a tissue with a first pattern of indicia corresponding to sampled anatomical locations of said tissue and a plurality of patterns of indicia corresponding to displacement of said anatomical locations during a selected time interval; and generating a set of parameter signals representing displacement of said anatomical locations corresponding to said first pattern of indicia, wherein said patterns of indicia comprise sets of tagging symbols.

22. The method of claim 21, wherein said indicia provide real time visualization of said displacement.

* * * * *

UNITED STATES PATENT AND TRADEMARK OFFICE
CERTIFICATE OF CORRECTION

PATENT NO. : 6,863,655 B2
DATED : March 8, 2005
INVENTOR(S) : Bjaerum et al.

It is certified that error appears in the above-identified patent and that said Letters Patent is hereby corrected as shown below:

Column 5,
Line 37, Equation 1, delete "$S_{i=T}*$" and substitute therefore -- $S_i = T*$ --.

Column 6,
Line 20, Equation 1, delete "$S_iT*$" and substitute therefore -- $S_i = T*$ --.

Column 8,
Line 26, delete "JYC, LVR" and substitute therefore -- IVC, IVR --.

Signed and Sealed this

Twenty-third Day of August, 2005

JON W. DUDAS
*Director of the United States Patent and Trademark Office*